(12) United States Patent
Dietsche et al.

(10) Patent No.: US 7,164,037 B2
(45) Date of Patent: Jan. 16, 2007

(54) ENZYMATIC PRODUCTION OF (METH)ACRYLIC ESTERS THAT CONTAIN URETHANE GROUPS

(75) Inventors: Frank Dietsche, Schriesheim (DE); Dietmar Haering, Schriesheim (DE); Eva Wagner, Speyer (DE); Reinhold Schwalm, Wachenheim (DE); Heinz-Peter Rink, Muenster (DE); Erich Beck, Ladenburg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/536,968

(22) PCT Filed: Dec. 4, 2003

(86) PCT No.: PCT/EP03/13689

§ 371 (c)(1),
(2), (4) Date: May 31, 2005

(87) PCT Pub. No.: WO2004/050888

PCT Pub. Date: Jun. 17, 2004

(65) Prior Publication Data

US 2006/0084779 A1    Apr. 20, 2006

(30) Foreign Application Priority Data

Dec. 5, 2002    (DE) ................ 102 57 094

(51) Int. Cl.
*C07C 261/00*    (2006.01)
*C08G 73/00*    (2006.01)

(52) U.S. Cl. ............ 560/132; 560/157; 528/370

(58) Field of Classification Search ........... 560/132, 560/157; 528/370
See application file for complete search history.

(56) References Cited

U.S. PATENT DOCUMENTS 3,718,692 A    2/1973  Durvasula 5,240,835 A    8/1993  Pettrone et al.

FOREIGN PATENT DOCUMENTS

| DE | 2 027 465 | 12/1971 |
|---|---|---|
| EP | 036 813 | 9/1981 |
| EP | 263 749 | 4/1988 |
| EP | 999 229 | 5/2000 |
| EP | 999 230 | 5/2000 |
| EP | 1 043 351 | 10/2000 |
| EP | 1 162 218 | 12/2001 |
| JP | 2001-040039 | 2/2001 |
| WO | 98/50345 | 11/1998 |
| WO | WO 9850345 A1 * | 11/1998 |

OTHER PUBLICATIONS

Regina Derango, Yi-Fong Wang, Ross Dowbenko, Lin-chang Chiang The Lipase-Catalysed Synthesis of Carbamoyloxyethyl Methacrylate Biotechnology Letters vol. 16, No. 3, Mar. 1994, pp. 241-246.*
Regina Derango et al., "The lipase-catalyzed synthesis of carbamoyloxyethyl methacrylate", Biotechnology Letters, vol. 16, No. 3, pp. 241-246 Mar. 1994.
Joachim Probst et al., "Homo- und copolymerisation von N, N-disubstitulerten carbamoyloxyalkylacrylaten und—methacrylaten", Maromolecular Chemistry, vol. 177, pp. 2681-2695 1976.
Adam B. Hajjar et al., "Preparation of monomeric acrylic ester intermediates using lipase catalysed transesterifications in organic solvents", Biotechnology Letters, vol. 12, No. 11, pp. 825-830 1990.

* cited by examiner

*Primary Examiner*—Samuel A Barts
*Assistant Examiner*—Lalitha Nagubandi
(74) *Attorney, Agent, or Firm*—Oblon, Spivak, McClelland, Maier & Neustadt, P.C.

(57) ABSTRACT

Enzymatic preparation of (meth)acrylic esters containing urethane groups, and their use in radiation-curable compositions.

12 Claims, No Drawings

ENZYMATIC PRODUCTION OF (METH)ACRYLIC ESTERS THAT CONTAIN URETHANE GROUPS

DESCRIPTION

The present invention relates to a process for preparing (meth)acrylic esters containing urethane groups and to the use thereof in radiation-curable coating compositions.

(Meth)acrylic esters are generally prepared by acid- or base-catalyzed esterification or transesterification of (meth) acrylic acid or other (meth)acrylic esters with alcohols at temperatures from 40 to well above 100° C. In view of the high temperatures it is necessary to add large amounts of polymerization inhibitors in order to suppress any unwanted polymerization of the monomers. This often produces complex and occasionally colored product mixtures. In order to remove colorations and unreacted reactants the product mixtures are worked up by expensive alkaline washes. The washing process is lengthy and costly, since partially esterified products in particular are slow to extract and separate.

The preparation of (meth)acrylates containing urethane groups by conventional acid-catalyzed esterification, moreover, is difficult, because urethane groups are acid sensitive.

JP-A 2001-40039 describes (meth)acrylic esters that contain carbamate groups and are prepared by way of an acid-catalyzed esterification.

A disadvantage of the process described is that the purity of the resultant product is only 75.9% for a mass balance of 95%.

EP-A1 36 813 describes the two-stage preparation of N-substituted acrylates containing carbamate groups by reacting multiply hydroxyalkylated acrylates with isocyanates.

A disadvantage of the process described is the restriction to those substrates which are available in the form of isocyanates. For example, N,N-disubstituted carbamates cannot be prepared by this process, and nor can those with nitrogen substituents which carry isocyanate-reactive groups. For reaction with the isocyanate, moreover, toxic tin compound catalysts are required.

The preparation of (meth)acrylic esters by an enzymatic esterification or transesterification is known.

Hajjar et al. in *Biotechnol. Lett.* 1990, 12, 825–830 describe the enzymatic transesterification of cyclic and open-chain alkanediols with ethyl acrylate using a lipase from *Chromobacterium viscosum*. The reactions proceed with an 18-fold molar excess of the alkyl acrylate over the diol in a solvent-free system. This produces mixtures of monoacrylates and diacrylates.

U.S. Pat. No. 5,240,835 describes the transesterification of alkyl acrylates with alcohols with catalysis by a biocatalyst from *Corynebacterium oxydans*. Depicted by way of example therein is the reaction of a 96-fold molar excess of ethyl acrylate with 2,2-dimethyl-1,3-propanediol. A yield of only 21% was obtained after 3 days at 30° C.

Derango et al. in *Biotechnol. Lett.* 1994, 16, 241–246 describe the lipase-catalyzed preparation of carbamoyloxyethyl methacrylate by transesterification of 2-hydroxyethyl carbamate with vinyl methacrylate. Complete reaction is achieved by the specific vinyl methacrylate reactant, since vinyl alcohol liberated is removed from the reaction equilibrium in the form of acetaldehyde. A disadvantage of this process is that vinyl methacrylate is not commercially available.

The use of (meth)acrylic esters containing urethane groups in radiation-curable coating compositions is known from EP-A1 263 749.

It is an object of the present invention to provide a process by which (meth)acrylic esters containing urethane groups can be prepared in high conversions and high purities from simple reactants which are classed as less toxicologically objectionable than vinyl methacrylate. The synthesis ought to run under mild conditions, to give products having a low color number and viscosity.

We have found that this object is achieved by a process for preparing (meth)acrylic esters (F) containing urethane groups by c) reacting an alcohol (C) containing urethane groups with (meth)acrylic acid or with an ester of (meth)acrylic acid with a saturated alcohol (D), and d) if desired, working up the reaction mixture from c), the reaction c) being conducted in the presence of an enzyme (E).

The process of the invention allows (meth)acrylic esters containing urethane groups to be prepared in high chemical and space/time yield and under mild conditions. With the process of the invention it is possible, advantageously, to prepare (meth)acrylic esters, containing urethane groups, that have less coloration and/or lower viscosity than in accordance with the prior art. As a further advantage it is possible to reduce the use of polymerization inhibitors, and with particular advantage they can be dispensed with entirely.

Urethane groups for the purposes of this document are O-substituted and N-unsubstituted, monosubstituted or disubstituted structural elements of the formula >N—C (=O)—O—.

(Meth)acrylic acid in this document stands for methacrylic acid and acrylic acid, preferably for acrylic acid.

Alcohols (C) containing urethane groups are compounds which comprise at least one urethane group, preferably from 1 to 10, more preferably from 1 to 5, very preferably 1 or 2, and in particular one urethane group, and also at least one hydroxyl group (—OH), preferably from 1 to 10, more preferably from 1 to 6, very preferably from 1 to 3, in particular 1 or 2, and especially one hydroxyl group.

Preferred alcohols (C) containing urethane groups have an average molar weight of from 105 to 800 000 g/mol, preferably from 120 to 25 000, more preferably from 200 to 5000, and very preferably from 400 to 4500 g/mol.

Particularly preferred alcohols (C) containing urethane groups are those obtainable by a) reacting an amine (A) with a carbonate (B), and b) if desired, working up the reaction mixture obtainable from a).

Amines in this case are ammonia, primary or secondary amines, and carbonates are O,O'-di-substituted carbonates having the structural element —O—C(=O)—O—.

Especially preferred alcohols (C) containing urethane groups are those obtainable by a reaction as per formula I in which R$^3$, R$^4$ independently are hydrogen, C$_1$–C$_{18}$ alkyl, C$_2$–C$_{18}$ alkyl uninterrupted or interrupted by one or more oxygen and/or sulfur atoms and/or by one or more substituted or unsubstituted imino groups, or are C$_2$–C$_{18}$ alkenyl, C$_6$–C$_{12}$ aryl, C$_5$–C$_{12}$ cycloalkyl or a five- to six-membered heterocycle containing oxygen, nitrogen and/or sulfur atoms, it being possible for each of the radicals stated to be substituted by aryl, alkyl, aryloxy, alkyloxy, heteroatoms and/or heterocycles, or are a group of the formula —[X$_i$]$_k$—H, Y is C$_2$–C$_{20}$ alkylene or C$_5$–C$_{12}$ cycloalkylene or is C$_2$–C$_{20}$ alkylene which is interrupted by one or more oxygen and/or sulfur atoms and/or by one or more substituted or unsubstituted imino groups and/or by one or more cycloalkyl, —(CO)—, —O(CO)O—, —(NH)(CO)O—, —O(CO)(NH)—, —O(CO)— or —(CO)O— groups, it being possible for each of the radicals stated to be substituted by aryl, alkyl, aryloxy, alkyloxy, heteroatoms and/or heterocycles, k is a number from 1 to 50, and X$_i$ for i=1 to k can be selected independently from the group consisting of —CH$_2$—CH$_2$—O—, —CH$_2$—CH$_2$—N(H)—, —CH$_2$—CH$_2$—CH$_2$—N(H)—, —CH$_2$—CH(NH$_2$)—, —CH$_2$—CH(NHCHO)—, —CH$_2$—CH(CH$_3$)—O—, —CH(CH$_3$)—CH$_2$—O—, —CH$_2$—C(CH$_3$)$_2$—O—, —C(CH$_3$)$_2$—CH$_2$—O—, —CH$_2$—CH$_2$—CH$_2$—O—, —CH$_2$—CH$_2$—CH$_2$—CH$_2$—O—, —CH$_2$—CHVin-O—, —CHVin-CH$_2$—O—, —CH$_2$—CHPh—O—, and —CHPh—CH$_2$—O—, where Ph stands for phenyl and Vin stands for vinyl.

R$^3$ and R$^4$ can also together form a ring.

Preferably R$^3$ and R$^4$ independently are hydrogen, C$_1$–C$_{12}$ alkyl, C$_5$–C$_6$ cycloalkyl or a group of the formula —[X$_i$]$_k$—H; with particular preference R$^3$ and R$^4$ independently are hydrogen, C$_1$–C$_4$ alkyl, C$_5$–C$_6$ cycloalkyl or a group of the formula —[X$_i$]$_k$—H; and very preferably R$^3$ and R$^4$ are hydrogen, C$_1$–C$_4$ alkyl, or a group of the formula —[X$_i$]$_k$—H. In particular, one of the radicals R$^3$ and R$^4$ is hydrogen and the other is C$_1$–C$_4$ alkyl, or a group of the formula —[X$_i$]$_k$—H.

Y is preferably C$_2$–C$_{10}$ alkylene, more preferably C$_2$–C$_6$ alkylene, very preferably C$_2$–C$_4$ alkylene, in particular C$_2$–C$_3$ alkylene, and especially C$_2$ alkylene, it being possible for each of the radicals stated to be substituted by aryl, alkyl, aryloxy, alkyloxy, heteroatoms and/or heterocycles.

k is preferably 1 to 30, more preferably 1 to 20, very preferably 1 to 10, and in particular 1 to 5.

Preferred X$_1$ are —CH$_2$—CH$_2$—O—, —CH$_2$—CH$_2$—N(H)—, —CH$_2$—CH$_2$—CH$_2$—N(H)—, —CH$_2$—CH(NH$_2$)—, —CH$_2$—CH(NHCHO)—, —CH$_2$—CH(CH$_3$)—O— and —CH(CH$_3$)—CH$_2$—O—, more preferably —CH$_2$—CH$_2$—O—, —CH$_2$—CH$_2$—N(H)—, —CH$_2$—CH$_2$—CH$_2$—N(H)— and —CH$_2$—CH(NH$_2$)—, very preferably —CH$_2$—CH$_2$—O—, —CH$_2$—CH$_2$—N(H)—, and —CH$_2$—CH$_2$—CH$_2$—N(H)—.

Examples of R$^3$ and/or R$^4$ are hydrogen, methyl, ethyl, isopropyl, n-propyl, n-butyl, isobutyl, sec-butyl, tert-butyl, n-hexyl, n-heptyl, n-octyl, n-decyl, n-dodecyl, n-tetradecyl, n-hexadecyl, n-octadecyl, n-eicosyl, 2-ethylhexyl, cyclopentyl, cyclohexyl, cyclooctyl, cyclododecyl, 2-hydroxyethyl, 2-hydroxypropyl, 1-hydroxypropyl, 5-hydroxy-3-oxapentyl, 8-hydroxy-3,6-dioxaoctyl or 11-hydroxy-3,6,9-trioxaundecyl.

Examples of Y are 1,2-ethylene, 1,2-propylene, 1,1-dimethyl-1,2-ethylene, 1-hydroxymethyl-1,2-ethylene, 2-hydroxy-1,3-propylene, 1,3-propylene, 1,4-butylene, 1,6-hexylene, 2-methyl-1,3-propylene, 2-ethyl-1,3-propylene, 2,2-dimethyl-1,3-propylene, and 2,2-dimethyl-1,4-butylene, preferably 1,2-ethylene, 1,2-propylene, and 1,3-propylene, more preferably 1,2-ethylene and 1,2-propylene, and very preferably 1,2-ethylene.

Exemplary amines (A) are ammonia, methylamine, dimethylamine, ethylamine, diethylamine, isopropylamine, diisopropylamine, n-butylamine, di-n-butylamine, tert-butylamine, monoethanolamine, diethanolamine, propanolamine, dipropanolamine, piperidine, piperazine, pyrrolidine, cyclopentylamine, cyclohexylamine, aniline, ethylenediamine, diethylenetriamine, triethylenetetramine, tetraethylenepentamine, and polyethyleneimines having a weight-average molecular weight $M_w$ of from 200 to 25 000 g/mol, preferably from 400 to 8000, more preferably from 750 to 5000, and very preferably from 800 to 3000 g/mol. Polyethyleneimines which can be used in accordance with the invention have a ratio of primary:secondary:tertiary amine groups of for example 1:0.75–1.25:0.4–0.8. It is of course also possible to use polyethyleneimines with a higher molecular weight, going for example up to a molecular weight $M_w$ of 2 000 000, preferably up to 750 000; since, however, such polyethyleneimines are usually present in aqueous solution, the solvent should be removed and/or replaced by another prior to their use in the reaction according to the invention.

Examples of further possible amines (A) include hydrogenated polyacrylonitriles, straight-chain, branched or dendritic polymers containing amino functions, or at least partly hydrolyzed poly-N-vinylformamides.

Examples of straight-chain polymers containing amino functions are polyethylene glycols, polypropylene glycols, mixed polyalkylene oxides, poly-1,3-propanediols, poly-THF or alkoxylated polyols or monools in which at least one terminal hydroxyl group has been replaced by an amino group, and also amino-functionalized polyisobutenes, in each case with a weight-average molecular weight $M_w$ from 200 to 25 000 g/mol, preferably from 400 to 8000, more preferably from 750 to 5000, and very preferably from 800 to 3000 g/mol. Examples thereof are Jeffamines® from Huntsman Corp., Houston.

Branched polymers containing amino functions are for example described in WO 93/14147, p. 2, line 3–p. 6, line 14, whose preparation is described in the same document and also in WO 95/02008 and WO 97/23514, or those branched polymers whose preparation is described in WO 95/20619, and also the polyethylene glycol-polyethyleneimine block polymers described in Biomacromolecules, 2002, 3, 926–936.

Preferred branched polymers are, for example, the dendrimers prepared starting from 1,4-diaminobutane and obtainable by alternating Michael addition of acrylonitrile and hydrogenation of the nitrile group, including those of the 1st generation (Astramol® Am-4, from DSM, The Netherlands, CAS No. [120239-63-6]), of the 2nd generation (Astramol® Am-8, from DSM, The Netherlands, CAS No. [154487-83-9]), of the 3rd generation (Astramol® Am-16, CAS No. [154487-85-1]), of the 4th generation (Astramol® Am-32, CAS No. [163611-04-9]) or of the 5th generation (Astramol® Am-64, CAS No. [163611-05-0]).

At least partly hydrolyzed poly-N-vinylformamides are for example described in EP B1 71 050, p. 1, line 31 to p. 4, line 54. Preferred hydrolyzed poly-N-vinylformamides are those having a K value (in accordance with Fikentscher, measured in 0.5% strength by weight aqueous sodium chloride solution at 25° C.) of between 10 and 110, with K values between 30 and 80 being particularly preferred, and having a degree of cleavage (degree of hydrolysis of the formyl group) of from 10 to 100 mol %, more preferably from 10 to 80, very preferably from 20 to 60, and with especial preference from 30 to 50 mol %.

Exemplary carbonates (B) are ethylene carbonate, 1,3-propylene carbonate, and 1,2-propylene carbonate.

The reaction of an amine (A) with a carbonate (B) is known per se, from U.S. Pat. No. 4,820,830, col. 4, line 44 to col. 5, line 9, for example, and is not restricted.

Typically the amine (A) and the carbonate (B) are reacted with one another in a stoichiometry of from 0.7 to 1.2 mol of amine: 1 mol of carbonate, preferably 0.8–1.2:1, more preferably 0.9–1.1:1, very preferably 0.95–1.1:1, and especially 1:1 mol/mol. The reaction takes place in general at a temperature of from 0 to 120° C., in particular from 20 to 100° C., more preferably from 30 to 80° C., and very preferably from 40 to 80° C. The reaction is generally over within 12 hours, preferably within from 15 minutes to 10 hours, more preferably in from 30 minutes to 8 hours, very preferably from 45 minutes to 6 hours, and in particular within 1 to 4 hours.

The total amine number to DIN 53176 of the reaction product should amount to not more than 200 mg KOH/g, preferably to not more than 100, and very preferably to not more than 80 mg KOH/g.

The reaction can be carried out without a solvent or in the presence of one, examples being alcohols, ethers, ketones, hydrocarbons, and water, but preferably without solvent.

The reaction mixture obtainable from a) can be worked up if desired in a further step b), by for example filtration, distillation, rectification, chromatography, treatment with ion exchangers, treatment with adsorbents, neutral, acidic and/or alkaline washing, stripping or crystallization.

One preferred embodiment of the present invention is constituted by (meth)acrylic esters containing urethane groups and obtainable by a) reacting a polyethyleneimine, a hydrogenated polyacrylonitrile, a branched polymer having amino functions or an at least partly hydrolyzed poly-N-vinylformamide having a weight-average molecular weight $M_w$ of from 200 to 1 000 000, preferably 200–750 000, more preferably 200–25 000, very preferably 400–8000, in particular 750–5000, and especially 800–3000 g/mol with a carbonate (B) at a temperature of from 0 to 120° C., b) if desired, working up the reaction mixture obtainable from a), c) reacting the reaction mixture from a) or b) with (meth)acrylic acid or with an ester of (meth)acrylic acid with a saturated alcohol (D) in the presence of an enzyme (E), and d) if desired, working up the reaction mixture from c).

Preference is given to reacting linear or branched polyethyleneimines, dendrimers containing amino functions, or at least partly hydrolyzed poly-N-vinylformamides, more preferably polyethyleneimines or dendrimers containing amino functions, and very preferably polyethyleneimines.

In step c) the alcohol containing urethane groups is transesterified or esterified with at least one (meth)acrylate or (meth)acrylic acid (D) in the presence of an enzyme (E) which catalyzes the (trans)esterification.

Compounds (D) can be (meth)acrylic acid or esters of (meth)acrylic acid with a saturated alcohol, preferably (meth)acrylic acid and the saturated $C_1$–$C_{10}$ alkyl esters thereof.

Saturated compounds for the purposes of this text are compounds without C—C multiple bonds (except of course for the C=C double bond in the (meth)acrylic units).

Examples of compounds (D) are (meth)acrylic acid and methyl, ethyl, n-butyl, isobutyl, n-octyl, and 2-ethylhexyl (meth)acrylate, 1,2-ethylene glycol di(meth)acrylate and mono(meth)acrylate, 1,4-butanediol di(meth)acrylate and mono(meth)acrylate, 1,6-hexanediol di(meth)acrylate and mono(meth)acrylate, trimethylolpropane tri(meth)acrylate, and pentaerythritol tetra(meth)acrylate.

Particular preference is given to (meth)acrylic acid and to methyl, ethyl, n-butyl, and 2-ethylhexyl (meth)acrylate, and very particular preference to methyl, ethyl, and n-butyl (meth)acrylate.

The enzymatic (trans)esterification with a (meth)acrylate or (meth)acrylic acid takes place in general at from 0 to 100° C., preferably from 20 to 80° C., more preferably from 20 to 70° C., and very preferably from 20 to 60° C.

Enzymes (E) which can be used in accordance with the invention are selected for example from hydrolases, esterases (E.C. 3.1.-.-), lipases (E.C. 3.1.1.3), glycosylases (E.C. 3.2.-.-) and proteases (E.C. 3.4.-.-) in free form or in a form in which they are chemically or physically immobilized on a carrier, preferably lipases, esterases or proteases. Particular preference is given to Novozyme 435 (lipase from *Candida antarctica* B) or lipase from *Aspergillus* sp., *Aspergillus niger* sp., *Mucor* sp., *Penicillium cyclopium* sp., *Geotricum candidum* sp., *Rhizopus javanicus, Burkholderia* sp., *Candida* sp., *Pseudomonas* sp., or porcine pancreas, very particular preference to lipase from *Candida antarctica* B or from *Burkholderia* sp.

The enzyme content of the reaction medium lies generally in the range from about 0.1 to 10% by weight, based on the sum of the components (C) and (D) employed. The reaction time depends among other things on the temperature, on the amounts and activity of the enzyme catalyst used, and on the required conversion, and also on the alcohol containing urethane groups. The reaction time is preferably adapted so that the conversion of all hydroxyl functions originally present in the alcohol (C) is at least 70%, preferably at least 80%, more preferably at least 90% and very preferably at least 95%. For this a time of from 1 to 48 hours and preferably from 1 to 12 hours is generally sufficient.

The molar ratio of (meth)acrylic acid compound (D) (based on the (meth)acrylic units) to alcohol (C) containing urethane groups (based on hydroxyl groups) can vary within a wide range, such as in a ratio of from 100:1 to 1:1, preferably from 50:1 to 1:1, more preferably from 20:1 to 1:1, and very preferably from 10:1 to 1:1.

The reaction can proceed in organic solvents or mixtures thereof or without the addition of solvents. The reaction mixtures are generally substantially anhydrous (i.e., with addition of less than 10%, preferably less than 5%, by volume of water).

The fraction of organic solvents is for example 0.01–90% by weight. Suitable organic solvents are those known for these purposes, examples being tertiary monools, such as $C_3$–$C_6$ alcohols, preferably tert-butanol or tert-amyl alcohol, pyridine, poly-$C_1$–$C_4$ alkylene glycol di-$C_1$–$C_4$-alkyl ethers, preferably polyethylene glycol di-$C_1$–$C_4$ alkyl ethers, such as 1,2-dimethoxyethane, diethylene glycol dimethyl ether, polyethylene glycol dimethyl ether 500, for example, $C_1$–$C_4$ alkylene carbonates, especially propylene carbonate, $C_3$–$C_6$ alkyl acetic esters, especially tert-butyl acetate, THF, toluene, 1,3-dioxolane, acetone, isobutyl methyl ketone, ethyl methyl ketone, 1,4-dioxane, tert-butyl methyl ether, cyclohexane, methylcyclohexane, toluene, hexane, dimethoxymethane, 1,1-dimethoxyethane, acetonitrile, and the single-phase or multiphase mixtures thereof. It can be advantageous to separate off water of reaction by means of a binary or ternary heteroazeotrope which boils as close as possible to the temperature optimum of the enzyme used, an example being ethyl methyl ketone/hexane/water. The water removed azeotropically can then be removed by phase separation or membrane vapor separation.

An option is to add aqueous solvents to the organic solvents, to produce reaction solutions which depending on the organic solvent take the form of a single phase or multiple phases. Examples of aqueous solvents are water and also aqueous dilute (e.g., 10 to 100 mM) buffers, with a pH for example in the range from about 6 to 8, such as potassium phosphate buffer or TRIS HCl buffer, for example.

The water fraction in the reaction mixture is generally 0–10% by volume. Preferably the reactants are used without pretreatment (drying, water doping).

The substrates are alternatively in solution, in suspension as solids, or in emulsion in the reaction medium. The initial concentration of the reactants is preferably in the range from about 0.1 to 20 mol/l, in particular from 0.15 to 10 mol/l or from 0.2 to 5 mol/l.

The reaction can take place continuously, in a tube reactor or in a cascade of stirred reactors, for example, or batchwise.

The reaction can be carried out in all reactors that are suitable for such reaction. Reactors of this kind are known to the skilled worker. The reaction takes place preferably in a stirred tank reactor or in a fixed bed reactor.

The reaction mixture can be mixed by a variety of methods. There is no need for special stirring equipment. The reaction medium can be single phase or have a plurality of phases and the reactants are dissolved, suspended or emulsified therein, introduced into the reaction vessel together where appropriate with the molecular sieve, and admixed with the enzyme preparation at the beginning of the reaction and also, where appropriate, one or more times during the course of the reaction. During the reaction the temperature is set at the desired level and can be raised or lowered if desired during the course of the reaction.

If the reaction is carried out in a fixed bed reactor the reactor is preferably packed with immobilized enzymes, with the reaction mixture being pumped through a column packed with the enzyme. It is also possible to carry out the reaction in a fluidized bed, with the enzyme being used in immobilized form on a carrier. The reaction mixture can be pumped continuously through the column, in which case the residence time and hence the desired conversion can be controlled via the flow rate. Another possibility is to pump the reaction mixture through a column in circulation, in which case it is possible at the same time to remove the water of reaction and/or the liberated alcohol by distillation, under reduced pressure where appropriate.

The removal of the water of reaction or of alcohols which are liberated from the alkyl acrylates in the case of a transesterification takes place continuously or gradually in a manner known per se, for example by reduced pressure, azeotropic removal, absorption, pervaporation, and diffusion via membranes.

Means suitable for this purpose include preferably molecular sieves (pore size in the region of about 3–10 Angströms, for example), separation by distillation, or separation with the aid of suitable semipermeable membranes.

After the end of the reaction the reaction mixture obtainable from c) can be used further without additional workup or if required can be worked up in a further step d).

d) In general only the enzyme used and any molecular sieve used are separated from the reaction mixture and the reaction product is separated from any organic solvent used.

Enzyme is generally separated off by filtration, absorption, centrifugation or decanting. The enzyme separated off can then be employed for further reactions.

Separation from organic solvent takes place in general by distillation, by rectification or, in the case of solid reaction products, by filtration.

For further workup of the reaction product it is also possible to carry out chromatography.

Preferably in step d), however, only the enzyme used and any solvent used are separated off.

The reaction conditions for the enzymatic esterification or transesterification are mild. The low temperatures and other mild conditions prevent the formation in step c) of byproducts which might otherwise originate, for example, from chemical catalysts or as a result of unwanted free-radical polymerization of the (meth)acrylate or (meth)acrylic acid used, which can otherwise be prevented only by adding stabilizers. In the reaction regime according to the invention it is possible to add stabilizer to the (meth)acrylic compound (D) above and beyond the storage stabilizer which is present in any case, examples of such additional stabilizers being hydroquinone monomethyl ether, phenothiazine, phenols, such as 2-tert-butyl-4-methylphenol or 6-tert-butyl-2,4-dimethylphenol, or N-oxyls, such as 4-hydroxy-2,2,6,6-tetramethylpiperidine-N-oxyl or 4-oxo-2,2,6,6-tetramethylpiperidine-N-oxyl, in amounts of from 50 to 2000 ppm, for example. The (trans)esterification is conducted advantageously in the presence of an oxygen-containing gas, preferably air or air/nitrogen mixtures. In addition there is no difficulty in separating the enzyme catalyst from the end product. Moreover, generally speaking, there is no substantial discernible cleavage of the urethane groups as a result of enzymatic hydrolysis: the level of byproducts is generally less than 10%, preferably less than 5%.

By the process of the invention it is possible in one particularly preferred embodiment to obtain (meth)acrylic esters (F) containing urethane groups, of the formula (II)

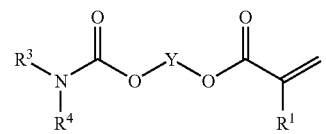

in which
$R^3$ and $R^4$ are as defined above,
Y is selected from 1,2-ethylene, 1,2-propylene, 1,1-dimethyl-1,2-ethylene, 1-hydroxymethyl-1,2-ethylene, 2-hydroxy-1,3-propylene, 2-hydroxy-1,3-propylene, 1,3-propylene, 1,4-butylene, 1,6-hexylene, 2-methyl-1,3-propylene, 2-ethyl-1,3-propylene, 2,2-dimethyl-1,3-propylene, and 2,2-dimethyl-1,4-butylene, or

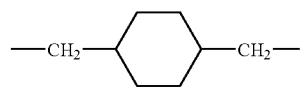

or 1,2-, 1,3- or 1,4-cyclohexylene,
$R^1$ is hydrogen or methyl, preferably hydrogen, with the proviso that at least one of the radicals $R^3$ and $R^4$ is other than hydrogen.

In radiation-curable coating compositions these (meth)acrylic esters containing urethane groups effect a sharp increase in the scratch resistance and elasticity while being of low viscosity, thereby making the compounds of the formula (II) valuable constituents of radiation-curable coating compositions.

An advantage of the process of the invention is that substantially complete conversions can be achieved with simple (meth)acrylic compounds (D) on account of the fact that the reaction equilibrium can be shifted without the need to use specialty reactants such as vinyl methacrylate for example.

The (meth)acrylic esters containing urethane groups that are obtainable from stages c) and d) respectively can be used with advantage as comonomers in, for example, poly(meth) acrylates or as reactive diluents in radiation-curable and/or dual cure poly(meth)acrylates. Poly(meth)acrylates of this kind are suitable for use as binders in radiation-curable or dual cure coating materials.

Coatings obtainable in this way feature very high scratch resistance, hardness, chemical resistance, elasticity, and adhesion, on both hydrophilic and hydrophobic substrates.

The (meth)acrylic esters containing urethane groups that are prepared in accordance with the invention can also be used advantageously, on account of their relatively low coloration, in a thermally induced (free-radical) (co)polymerization.

Examples of monomers with which the urethane-group-containing (meth)acrylic esters prepared in accordance with the invention can be copolymerized by way of example include $C_1$–$C_{20}$ alkyl (meth)acrylates, vinylaromatics having up to 20 carbon atoms, vinyl esters of carboxylic acids comprising up to 20 carbon atoms, ethylenically unsaturated nitriles, vinyl ethers of alcohols comprising 1 to 10 carbon atoms, and aliphatic hydrocarbons having 2 to 8 carbon atoms and 1 or 2 double bonds.

The term (meth)acrylic acid is used within this specification for acrylic acid and methacrylic acid.

Preferred alkyl (meth)acrylates are those with a $C_1$–$C_{10}$ alkyl radical, such as methyl methacrylate, methyl acrylate, n-butyl acrylate, ethyl acrylate, and branched alkyl derivatives such as 2-ethylhexyl acrylate.

Mixtures of the alkyl (meth)acrylates in particular are also suitable.

Vinyl esters of carboxylic acids having 1 to 20 carbon atoms are, for example, vinyl laurate, vinyl stearate, vinyl propionate, and vinyl acetate.

Examples of suitable vinylaromatic compounds include vinyltoluene, α-butylstyrene, 4-n-butylstyrene, 4-n-decylstyrene, and styrene, the latter being preferred.

Examples of nitriles are acrylonitrile and methacrylonitrile.

Suitable vinyl ethers include for example vinyl methyl ether, vinyl isobutyl ether, vinyl hexyl ether, and vinyl octyl ether.

Nonaromatic hydrocarbons having 2 to 8 carbons and one or two olefinic double bonds include butadiene, isoprene, and also ethylene, propylene, and isobutylene.

A frequent, though not the only, method of preparing such (co)polymers is that of free-radical or ionic (co)polymerization in a solvent or diluent.

The free-radical (co)polymerization of such monomers takes place for example in aqueous solution in the presence of polymerization initiators which under polymerization conditions disintegrate into free radicals, examples being peroxodisulfates, $H_2O_2$ redox systems or hydroxy peroxides, such as tert-butyl hydroperoxide or cumene hydroperoxide, for example. The (co)polymerization may be performed within a wide temperature range, if appropriate under reduced pressure or else under elevated pressure, in general at temperatures up to 100° C. The pH of the reaction mixture is commonly set in the range from 4 to 10.

The (co)polymerization can, however, also be carried out in a different way, known per se to the skilled worker, continuously or batchwise, in the form, for example, of a solution, precipitation, water-in-oil emulsion, inverse emulsion, suspension or inverted suspension polymerization.

In this case the monomer/the monomers is or are (co) polymerized using free-radical polymerization initiators, examples being azo compounds which disintegrate into free radicals, such as 2,2'-azobis(isobutyronitrile), 2,2'-azobis(2-amidinopropane)hydrochloride or 4,4'-azo-bis(4'-cyanopentanoic acid) or dialkyl peroxides, such as di-tert-amyl peroxide, aryl alkyl peroxides, such as tert-butyl cumyl peroxide, alkyl acyl peroxides, such as tert-butyl peroxy-2-ethylhexanoate, peroxydicarbonates, such as di(4-tert-butylcyclohexyl)peroxydicarbonate, or hydroperoxides.

The stated compounds are used mostly in the form of aqueous solutions or aqueous emulsions, the lower concentration being determined by the amount of water that is acceptable in the (co)polymerization, and the upper concentration by the solubility of the respective compound in water.

Examples of solvents or diluents which can be used include water, alcohols, such as methanol, ethanol, n- or isopropanol, n- or isobutanol, or ketones, such as acetone, ethyl methyl ketone, diethyl ketone or isobutyl methyl ketone. Particular preference is given to a polar solvents such as, for example, xylene and its isomer mixtures, and to Shellsol® A and solvent naphtha.

In one preferred embodiment the monomers are premixed and initiator is added with further additions, if appropriate, in solution in solvent. One particularly preferred embodiment is described in WO 01/23484 on page 10, line 3 to line 24 therein in particular.

If appropriate the (co)polymerization can be carried out in the presence of polymerization regulators, such as hydroxylammonium salts, chlorinated hydrocarbons and thio compounds, for example, such as tert-butyl mercaptan, thioglycolic acid ethylacrylic ester, mercaptoethynol, mercaptopropyltrimethoxysilane, dodecyl mercaptan, tert-dodecyl mercaptan or alkali metal hypophosphites. In the case of the (co)polymerization it is possible for these regulators to be used in amounts, for example, of 0 to 0.8 parts by weight, based on 100 parts by weight of the monomers to be (co)polymerized, and they reduce the molar mass of the (co)polymer which forms.

In the course of the emulsion polymerization it is possible to use dispersants, ionic and/or nonionic emulsifiers and/or protective colloids, or stabilizers, as surface-active compounds. Suitable such compounds include both the protective colloids that are commonly used for carrying out emulsion polymerizations, and emulsifiers.

Examples of suitable protective colloids include polyvinyl alcohols, cellulose derivatives or vinyl-pyrrolidone copolymers. A detailed description of further suitable protective colloids is found in Houben-Weyl, Methoden der organischen Chemie, volume XIV/1, Makromolekulare Stoffe [Macromolecular compounds], Georg-Thieme-Verlag, Stuttgart, 1969, pp. 411 to 420. It is of course also possible to use mixtures of emulsifiers and/or protective colloids. As dispersants it is preferred to use exclusively emulsifiers, whose relative molecular weights, unlike those of the protective colloids, are usually below 1000. They may be anionic, cationic or nonionic in nature. Where mixtures of surface-active substances are used it is of course necessary for the individual components to be compatible with one another, something which in case of doubt can be checked by another means of a few preliminary tests. Generally speaking, anionic emulsifiers are compatible with one another and with nonionic emulsifiers.

The same also applies to cationic emulsifiers, whereas anionic and cationic emulsifiers are mostly incompatible with one another. Examples of customary emulsifiers include ethoxylated mono-, di- and tri-alkylphenols (EO degree: 3 to 100,: $C_4$ to $C_{12}$), ethoxylated fatty alcohols (EO degree: 3 to 100, alkyl radical: $C_8$ to $C_{18}$), and also alkali metal salts and ammonium salts of alkyl sulfates (alkyl radical: $C_8$ to $C_{16}$), of sulfuric monoesters with ethoxylated alkylphenols (EO degree: 3 to 100, alkyl radical: $C_4$ to $C_{12}$), of alkylsulfonic acids (alkyl radical: $C_{12}$ to $C_{18}$) and of alkylarylsulfonic acids (alkyl radical: $C_9$ to $C_{18}$). Further suitable emulsifiers such as sulfosuccinic esters are found in Houben-Weyl, Methoden der organischen Chemie, volume XIV/1, Makromolekulare Stoffe, Georg-Thieme-Verlag, Stuttgart, 1961, pages 192 to 208.

In general the amount of dispersant used is 0.5 to 6%, preferably 1 to 3%, by weight based on the monomers for free-radical polymerization.

Examples of (meth)acrylate-containing dispersions are n-butyl acrylate/acrylonitrile dispersions, which are employed as adhesives, n-butyl acrylate/butadiene/styrene The polymer dispersions in which (meth)acrylic esters containing urethane groups and prepared in accordance with the invention are used may additionally be chemically and/or physically deodorized.

The copolymers obtainable with the (meth)acrylic esters containing urethane groups and prepared in accordance with the invention generally have a relatively low color number, which is advantageous in the coatings field. The copolymers described can then be reacted in a manner known per se with, for example, amino resins, such as melamine, for example, to form crosslinked film-forming resins, as is described, for example, in EP 738740 or EP 675141.

The present invention further provides accordingly for the use of the (meth)acrylic esters containing urethane groups prepared by the process of the invention as reactive diluents or binders in radiation-curable or dual cure coating compositions, preferably in top coats, more preferably in transparent clearcoat materials. Of course the (meth)acrylic esters containing urethane groups prepared in accordance with the invention can also be used as monomers in polymerizations, together where appropriate with other polymerizable monomers, such as (meth)acrylic acid, (meth)acrylic esters, styrene, butadiene, acrylonitrile, vinyl acetate, N-vinylpyrrolidone, 4-hydroxybutyl vinyl ether or N-vinylformamide, for example.

By dual cure is meant that the coating compositions are curable thermally and with actinic radiation. Actinic radiation for the purposes of the present invention is electromagnetic radiation such as visible light, UV radiation or X-rays, especially UV radiation, and corpuscular radiation such as electron beams.

Radiation-curable binders are those curable by means of actinic radiation as defined above, particularly by means of UV radiation.

The present invention further provides coating formulations comprising the (meth)acrylic esters containing urethane groups that are obtainable by the process of the invention. These esters can be used in both basecoat and topcoat materials. Because of their particular properties, such as that of increasing the scratch resistance and elastic- ity, and of reducing the viscosity, particularly in the case of branched polyacrylates, of a radiation-cured clearcoat, their use in topcoats is preferred.

Besides the (meth)acrylic esters (F) containing urethane groups that are obtainable by the process of the invention, a radiation-curable composition of the invention may include the following additional components:
(G) at least one polymerizable compound containing two or more copolymerizable, ethylenically unsaturated groups,
(H) if desired, reactive diluents,
(I) if desired, photoinitiator, and
(J) if desired, further typical coatings additives.

Suitable compounds (G) include radiation-curable, free-radically polymerizable compounds containing two or more copolymerizable, ethylenically unsaturated groups.

Compounds (G) are preferably vinyl ether compounds or (meth)acrylate compounds, particular preference being given in each case to the acrylate compounds, i.e., the derivatives of acrylic acid.

Preferred vinyl ether compounds and (meth)acrylate compounds (G) contain from 2 to 20, more preferably from 2 to 10, and very preferably from 2 to 6 copolymerizable, ethylenically unsaturated double bonds.

Particularly preferred compounds (G) are those having an ethylenically unsaturated double bond content of 0.1–0.7 mol/100 g, very preferably 0.2–0.6 mol/100 g.

The number-average molecular weight $M_n$ of the compounds (G) unless otherwise stated is preferably below 15 000, more preferably 300–12 000, very preferably from 400 to 5000, and in particular 500–3000 g/mol (as determined by gel permeation chromatography using polystyrene standards and tetrahydrofuran eluent).

(Meth)acrylate compounds include (meth)acrylic esters and especially acrylic esters and also vinyl ethers of polyfunctional alcohols, particularly those which apart from the hydroxyl groups contain no other functional groups or, if any at all, then ether groups. Examples of such alcohols include difunctional alcohols, such as ethylene glycol, propylene glycol, and their more highly condensed counterparts, such as diethylene glycol, triethylene glycol, dipropylene glycol, tripropylene glycol etc., 1,2-, 1,3-, or 1,4-butanediol, 1,5-pentanediol, 1,6-hexanediol, 3-methyl-1,5-pentanediol, neopentyl glycol, alkoxylated phenolic compounds, such as ethoxylated and/or propoxylated bisphenols, 1,2-, 1,3-, or 1,4-cyclohexanedimethanol, alcohols with a functionality of 3 or more, such as glycerol, trimethylolpropane, butanetriol, trimethylolethane, pentaerythritol, ditrimethylolpropane, dipentaerythritol, sorbitol, mannitol, and the corresponding alkoxylated alcohols, especially ethoxylated and/or propoxylated alcohols.

The alkoxylation products are obtainable conventionally by reacting the above alcohols with alkylene oxides, especially ethylene oxide or propylene oxide. The degree of alkoxylation per hydroxyl group is preferably from 0 to 10; that is, 1 mol of hydroxyl group can be alkoxylated with up to 10 mol of alkylene oxides.

Other (meth)acrylate compounds include polyester (meth)acrylates, which are the (meth)acrylic esters or vinyl ethers of polyesterols, and also urethane, epoxy or melamine (meth)acrylates.

Urethane (meth)acrylates are obtainable for example by reacting polyisocyanates with hydroxyalkyl (meth)acrylates and, where appropriate, chain extenders such as diols, polyols, diamines, polyamines or dithiols or polythiols.

The urethane (meth)acrylates preferably have a number-average molar weight $M_n$ of from 500 to 20 000, in particular from 750 to 10 000 and with particular preference from 750 to 3000 g/mol (as determined by gel permeation chromatography using polystyrene standards).

The urethane (meth)acrylates preferably contain from 1 to 5, more preferably from 2 to 4, mol of (meth)acrylic groups per 1000 g of urethane (meth)acrylate.

Epoxy (meth)acrylates are obtainable by reacting epoxides with (meth)acrylic acid. Examples of suitable epoxides include epoxidized olefins or glycidyl ethers, e.g., bisphenol A diglycidyl ether, or aliphatic glycidyl ethers, such as butanediol diglycidyl ether.

Melamine (meth)acrylates are obtainable by reacting melamine with (meth)acrylic acid or the esters thereof.

The epoxy (meth)acrylates and melamine (meth)acrylates preferably have a number-average molar weight $M_n$ of from 500 to 20 000, more preferably from 750 to 10 000 g/mol and very preferably from 750 to 3000 g/mol; the amount of (meth)acrylic groups is preferably from 1 to 5, more preferably from 2 to 4, per 1000 g of epoxy (meth)acrylate or melamine (meth)acrylate (as determined by gel permeation chromatography using polystyrene standards and tetrahydrofuran eluent).

Also suitable are carbonate (meth)acrylates containing on average preferably from 1 to 5, in particular from 2 to 4, very preferably 2 or 3 (meth)acrylic groups, and especially 2 (meth)acrylic groups.

The number-average molecular weight $M_n$ of the carbonate (meth)acrylates is preferably less than 3000 g/mol, more preferably less than 1500 g/mol, very preferably less than 800 g/mol (as determined by gel permeation chromatography with polystyrene standards and tetrahyrofuran solvent).

The carbonate (meth)acrylates are obtainable in a simple way by transesterification of carbonic esters with polyhydric, preferably dihydric, alcohols (diols, e.g., hexanediol) and subsequent esterification of the free OH groups with (meth)acrylic acid or else transesterification with (meth)acrylic esters, as described for example in EP-A 92 269. They are also obtainable by reacting phosgene, urea derivatives with polyhydric, e.g., dihydric, alcohols.

Suitable reactive diluents (compounds (H)) include radiation-curable, free-radically or cationically polymerizable compounds containing only one ethylenically unsaturated copolymerizable group.

Examples that may be mentioned include $C_1$–$C_{20}$ alkyl (meth)acrylates, vinylaromatics having up to 20 carbon atoms, vinyl esters of carboxylic acids containing up to 20 carbon atoms, ethylenically unsaturated nitriles, vinyl ethers of alcohols containing 1 to 10 carbon atoms, α,β-unsaturated carboxylic acids and their anhydrides, and aliphatic hydrocarbons having 2 to 8 carbon atoms and 1 or 2 double bonds.

Preferred alkyl (meth)acrylates are those with a $C_1$–$C_{10}$ alkyl radical, such as methyl methacrylate, methyl acrylate, n-butyl acrylate, ethyl acrylate, and 2-ethylhexyl acrylate.

Mixtures of the alkyl (meth)acrylates in particular are also suitable.

Vinyl esters of carboxylic acids having 1 to 20 carbon atoms are, for example, vinyl laurate, vinyl stearate, vinyl propionate, and vinyl acetate.

α,β-Unsaturated carboxylic acids and their anhydrides may for example be acrylic acid, methacrylic acid, fumaric acid, crotonic acid, itaconic acid, maleic acid or maleic anhydride, preferably acrylic acid.

Examples of suitable vinylaromatic compounds include vinyltoluene, α-butylstyrene, 4-n-butylstyrene, 4-n-decylstyrene, and styrene, the latter being preferred.

Examples of nitriles are acrylonitrile and methacrylonitrile.

Suitable vinyl ethers include for example vinyl methyl ether, vinyl isobutyl ether, vinyl hexyl ether, and vinyl octyl ether.

Nonaromatic hydrocarbons having 2 to 8 carbons and one or two olefinic double bonds include butadiene, isoprene, and also ethylene, propylene, and isobutylene.

It is additionally possible to use N-vinylformamide, N-vinylpyrrolidone, and N-vinylcaprolactam.

As photoinitiators (I) it is possible to use the photoinitiators known to the skilled worker, examples being those specified in "Advances in Polymer Science", Volume 14, Springer Berlin 1974 or in K. K. Dietliker, Chemistry and Technology of UV- and EB-Formulation for Coatings, Inks and Paints, Volume 3; Photoinitiators for Free Radical and Cationic Polymerization, P. K. T. Oldring (Eds), SITA Technology Ltd, London.

Suitable photoinitiators include, for example, monoacyl- or bisacylphosphine oxides Irgacure 819 (bis(2,4,6-trimethylbenzoyl)phenylphosphine oxide), as described for example in EP-A 7 508, EP-A 57 474, DE-A 196 18 720, EP-A 495 751 or EP-A 615 980, an example being 2,4,6-trimethylbenzoyldiphenylphosphine oxide (Lucirin® TPO) or ethyl 2,4,6-trimethylbenzoyl-phenylphosphinate, benzophenones, hydroxyacetophenones, phenylglyoxylic acid and its derivatives, or mixtures of these photoinitiators. Examples that may be mentioned include benzophenone, acetophenone, acetonaphthoquinone, methyl ethyl ketone, valerophenone, hexanophenone, α-phenylbutyrophenone, p-morpholinopropiophenone, dibenzosuberone, 4-morpholinobenzophenone, 4-morpholinodeoxybenzoin, p-diacetylbenzene, 4-aminobenzo-phenone, 4'-methoxyacetophenone, β-methylanthraquinone, tert-butylanthraquinone, anthraquinonecarboxylic esters, benzaldehyde, α-tetralone, 9-acetylphenanthrene, 2-acetylphenanthrene, 10-thioxanthenone, 3-acetylphenanthrene, 3-acetylindole, 9-fluorenone, 1-indanone, 1,3,4-triacetylbenzene, thioxanthen-9-one, xanthen-9-one, 2,4-dimethyl-thioxanthone, 2,4-diethylthioxanthone, 2,4-di-isopropylthioxanthone, 2,4-dichlorothioxanthone, benzoin, benzoin isobutyl ether, chloroxanthenone, benzoin tetrahydropyranyl ether, benzoin methyl ether, benzoin ethyl ether, benzoin butyl ether, benzoin isopropyl ether, 7H-benzoin methyl ether, benz[de]anthracen-7-one,1-naphthaldehyde, 4,4'-bis(dimethylamino)benzophenone, 4-phenylbenzophenone, 4-chlorobenzophenone, Michler's ketone, 1-acetonaphthone, 2-acetonaphthone, 1-benzoylcyclohexan-1-ol, 2-hydroxy-2,2-dimethylacetophenone, 2,2-di-methoxy-2-phenylacetophenone, 2,2-diethoxy-2-phenylacetophenone, 1,1-dichloroacetophenone, 1-hydroxyacetophenone, acetophenone dimethyl ketal, o-methoxybenzophenone, triphenylphosphine, tri-o-tolylphosphine, benz[a]anthracene-7,12-dione, 2,2-diethoxyacetophenone, benzil ketals, such as benzil dimethyl ketal, 2-methyl-1-[4-(methylthio)phenyl]-2-morpholinopropan-1-one, anthraquinones such as 2-methylanthraquinone, 2-ethylanthraquinone, 2-tert-butylanthraquinone, 1-chloroanthraquinone, 2-amylanthraquinone, and 2,3-butanedione.

Also suitable are non-yellowing or low-yellowing photoinitiators of the phenylglyoxalic ester type, as described in DE-A 198 26 712, DE-A 199 13 353 or WO 98/33761.

Of the photoinitiators stated preference is given to phosphine oxides, α-hydroxy ketones, and benzophenones.

In particular it is also possible to use mixtures of different photoinitiators.

The photoinitiators can be used alone or in combination with a photopolymerization promoter, of the benzoic acid type, amine type or a similar type, for example.

As further typical coatings additives (J) it is possible for example to use antioxidants, oxidation inhibitors, stabilizers, activators (accelerators), fillers, pigments, dyes, devolatilizers, gloss agents, antistatic agents, flame retardants, thickeners, thixotropic agents, leveling assistants, binders, antifoams, fragrances, surface-active agents, viscosity modifiers, plasticizers, plastificators, tackifying resins (tackifiers), chelating agents or compatibilizers.

As accelerators for the thermal aftercure it is possible, for example, to use tin octoate, zinc octoate, dibutyltin laurate or diaza[2.2.2]bicyclooctane.

Further possibilities for addition include one or more photochemically and/or thermally activable initiators, such as potassium peroxodisulfate, dibenzoyl peroxide, cyclohexanone peroxide, di-tert-butyl peroxide, azobisisobutyronitrile, cyclohexylsulfonyl acetyl peroxide, diisopropyl percarbonate, tert-butyl peroctoate or benzpinacol, and also, for example, those thermally activable initiators which have a half-life at 80° C. of more than 100 hours, such as di-t-butyl peroxide, cumene hydroperoxide, dicumyl peroxide, t-butyl perbenzoate, silylated pinacols, which are available commercially, for example, under the trade name ADDID 600 from Wacker, or hydroxyl-containing amine N-oxides, such as 2,2,6,6-tetramethylpiperidine-N-oxyl, 4-hydroxy-2,2,6,6-tetramethylpiperidine-N-oxyl, etc.

Further examples of suitable initiators are described in Polymer Handbook, 2nd ed., Wiley & Sons, New York.

Besides free-radically (co)polymerized (co)polymers, thickeners that are suitable include customary organic and inorganic thickeners such as hydroxymethylcellulose or bentonites.

As chelating agents it is possible to make use for example of ethylenediamine acetic acid and its salts and also β-diketones.

Suitable fillers include silicates, examples being silicates obtainable by hydrolysis of silicon tetrachloride, such as Aerosil® from Degussa, siliceous earth, talc, aluminum silicates, magnesium silicates, calcium carbonates, etc.

Suitable stabilizers include typical UV absorbers such as oxanilides, triazines, and benzotriazole (the latter available as Tinuvin® grades from Ciba Spezialitätenchemie) and benzophenones. These can be used alone or together with suitable free-radical scavengers, of which examples include sterically hindered amines such as 2,2,6,6-tetramethylpiperidine, 2,6-di-tert-butylpiperidine or derivatives thereof, such as bis(2,2,6,6-tetramethyl-4-piperidyl)sebacate. Stabilizers are used normally in amounts of from 0.1 to 5.0% by weight, based on the solid components present in the formulation.

Examples of stabilizers which are additionally suitable include N-oxyls, such as 4-hydroxy-2,2,6,6-tetramethylpiperidine-N-oxyl, 4-oxo-2,2,6,6-tetramethylpiperidine-N-oxyl, 4-acetoxy-2,2,6,6-tetramethylpiperidine-N-oxyl, 2,2,6,6-tetramethylpiperidine-N-oxyl, 4,4',4"-tris-(2,2,6,6-tetramethylpiperidine-N-oxyl) phosphite or 3-oxo-2,2,5,5-tetramethylpyrrolidine-N-oxyl, phenols and naphthols, such as p-aminophenol, p-nitrosophenol, 2-tert-butylphenol, 4-tert-butylphenol, 2,4-di-tert-butylphenol, 2-methyl-4-tert-butylphenol, 4-methyl-2,6-tert-butylphenol (2,6-tert-butyl-p-cresol) or 4-tert-butyl-2,6-dimethylphenol, quinones, such as hydroquinone or hydroquinone monomethyl ether, for example, aromatic amines, such as N,N-diphenylamine, N-nitrosodiphenylamine, phenylenediamines, such as N,N'-dialkyl-para-phenylenediamine, in which the alkyl radicals can be the same or different and consist each independently of from 1 to 4 carbon atoms and can be straight-chain or branched, hydroxylamines, such as N,N-diethylhydroxylamine, urea derivatives, such as urea or thiourea, phosphorus compounds, such as triphenylphosphine, triphenyl phosphite or triethyl phosphite, or sulfur compounds, such as diphenyl sulfide or phenothiazine, for example.

Typical compositions of radiation-curable compositions are for example
(F) 20–100% by weight, preferably 40–90%, more preferably 50–90%, and especially 60–80% by weight,
(G) 0–60% by weight, preferably 5–50%, more preferably 10–40%, and especially 10–30% by weight,
(H) 0–50% by weight, preferably 5–40%, more preferably 6–30%, and especially 10–30% by weight,
(I) 0–20% by weight, preferably 0.5–15%, more preferably 1–10%, and especially 2–5% by weight, and
(J) 0–50% by weight, preferably 2–40%, more preferably 3–30%, and especially 5–20% by weight,
with the proviso that (F), (G), (H), (I), and (J) together make 100% by weight.

The coating of the substrates takes place in accordance with customary methods known to the skilled worker, which involve applying at least one coating composition to the target substrate in the desired thickness and removing any volatile constituents of the coating composition, where appropriate with heating. This operation can if desired be repeated one or more times. Application to the substrate can be made in a known way, for example by spraying, troweling, knifecoating, brushing, rolling, roller coating, pouring, laminating, injection backmolding or coextruding. The coating thickness is generally in a range from about 3 to 1000 g/m$^2$ and preferably from 10 to 200 g/m$^2$.

Additionally disclosed is a method of coating substrates which involves applying the coating composition to the substrate and drying it where appropriate, curing it with electron beams or UV light under an oxygen-containing atmosphere or, preferably, under inert gas, and subjecting it to thermal treatment where appropriate at temperatures up to the level of the drying temperature and subsequently at temperatures up to 160° C., preferably between 60 and 160° C.

The method of coating substrates can also be performed by first applying the coating composition and then subjecting it to thermal treatment first at temperatures up to 160° C., preferably between 60 and 160° C., and then curing it with electron beams or UV light under oxygen or, preferably, under inert gas.

Curing of the films formed on the substrate may if desired take place exclusively by thermal means. In general, however, the coatings are cured both by exposure to high-energy radiation and thermally.

Instead of or in addition to the thermal cure, curing may also be effected by NIR radiation, which here is a term used for electromagnetic radiation in the wavelength range from 760 nm up to 2.5 μm, preferably from 900 to 1500 nm.

If two or more films of the coating material are applied over one another, it is possible if desired to carry out a thermal, NIR and/or radiation cure after each coating operation.

Suitable radiation sources for the radiation cure include for example low, medium or high pressure mercury lamps and also fluorescent tubes, pulsed emitters, metal halide lamps, electronic flash installations, which allow a radiation cure without photoinitiators, or excimer radiators. Radiation curing is effected by exposure to high-energy radiation, i.e. UV radiation or daylight, preferably light in the wavelength range λ of from 200 to 700 nm, more preferably from 200 to 500 nm and very preferably from 250 to 400 nm, or by irradiation with high-energy electrons (electron beams; 150 to 300 keV). The radiation sources used are, for example, high pressure mercury vapor lamps, lasers, pulsed lamps (flash light), halogen lamps or excimer radiators. The radiation dose normally sufficient for crosslinking in the case of UV curing is in the range from 80 to 3000 mJ/cm².

As will be appreciated it is also possible to use two or more radiation sources for the cure, e.g., from two to four.

These sources may also each emit in different wavelength ranges.

Irradiation can be performed where appropriate in the absence of oxygen, such as under an inert gas atmosphere. Suitable inert gases include preferably nitrogen, noble gases, carbon dioxide, or combustion gases. Irradiation may also take place with the coating composition covered with transparent media. Examples of transparent media are polymeric films, glass or liquids, such as water. Particular preference is given to irradiation in the manner described in DE-A1 199 57 900.

The invention further provides a method of coating substrates which involves
i) coating a substrate with a coating composition as described above,
ii) removing volatile constituents of the coating composition to form a film, under conditions in which the photoinitiator (I) essentially as yet does not form free radicals,
iii) if desired, irradiating the film formed in step ii) with high-energy radiation, the film undergoing initial cure, and then, if desired, mechanically working the article coated with the precured film or contacting the surface of the precured film with another substrate,
iv) completing the curing of the film thermally or using NIR radiation.

Steps iv) and iii) can also be carried out in the opposite order, i.e., the film can first be cured thermally or by NIR radiation and then using high-energy radiation.

Also provided by the present invention are substrates coated with a multicoat paint system of the invention.

The thickness of such a film to be cured as described can be from 0.1 µm to several mm, preferably from 1 to 2000 µm, more preferably from 5 to 1000 µm, very preferably from 10 to 500 µm, and in particular from 10 to 250 µm.

With particular preference the coating compositions of the invention are suitable as or in exterior coatings, i.e., in those applications which are exposed to daylight, preferably on buildings or parts of buildings, interior coatings, traffic markings, coatings on vehicles and aircraft. The coatings are employed in particular as wood, paper or plastics coatings, for woodblock flooring or furniture for example.

The examples which follow are intended to illustrate the properties of the invention without, however, restricting it.

EXAMPLES

Unless specified otherwise parts in this text are to be understood as meaning parts by weight.

Example 1

A mixture of 2.5 mol (220 g) of ethylene carbonate and 2.5 mol (180 g) of n-butylamine was stirred at 100° C. for 2 h. The reaction product was isolated by filtration to give 398 g of crude product (clear, colorless liquid).

The conversion as determined by GC was 99%.

Example 2

A mixture of 2.5 mol (220 g) of ethylene carbonate and 2.5 mol (247 g) of aminocyclohexane was stirred at room temperature at up to 120° C. for 4 h. The reaction product was isolated by filtration to give 465 g of crude product (clear, colorless liquid).

The conversion as determined by GC was 97%.

Example 3

16 g of a polyethyleneimine (0.2 mol of primary and secondary amino functions, Lupasol® FG, BASF AG) and 1 mol (88 g) of ethylene carbonate was stirred at 60–100° C. for 3 h. The mixture was filtered while still hot, and 23 g of crude product (yellowish solid) were obtained. A sample was taken, its OH number determined, and analyzed by GPC. The conversion of the primary and secondary amines was more than 90%, with a weight-average molar weight $M_w$ that had increased by about 650 g/mol on the starting product.

Example 4

A mixture of 0.5 mol (80 g) of the reaction mixture from example 1, 1.0 mol (86 g) of methyl acrylate and 2 g of Novozym 435 (lipase from *Candida antarctica* B) was stirred at 60° C. for 24 h. The enzyme was removed by filtration, methanol was removed in a rotary evaporator under reduced pressure and 86 g of crude product (clear, colorless liquid) were obtained.

The product is soluble in customary polyether, polyester, and urethane acrylates and can be admixed without clouding occurring.

A sample was taken, silylated, and analyzed by GC. The reaction mixture from example 1 had been converted to an extent of >97%.

Example 5

A mixture of 18.7 g (0.1 mol) of the reaction mixture from example 2, 1.0 mol (86 g) of methyl acrylate and 2 g of Novozym 435 (lipase from *Candida antarctica* B) was stirred at RT for 24 h. The enzyme was removed by filtration, methanol was removed in a rotary evaporator under reduced pressure, and 26 g of crude product (clear, colorless liquid) were obtained.

A sample was taken, silylated, and analyzed by GC. The reaction mixture from example 2 had undergone conversion to an extent of >95%.

Example 6

A mixture of 0.1 mol (OH equivalent, 7 g) of the reaction mixture from example 3, 1.0 mol (86.1 g) of methyl acrylate and 2.0 g of Novozym 435 (lipase from *Candida antarctica* B) was stirred at 60° C. for 24 h. The enzyme was removed by filtration, methanol was removed on a rotary evaporator under reduced pressure, and 15 g of crude product (yellowish solid) were obtained.

A sample was taken, its OH number was determined and it was analyzed by GPC. More than 95% of the alcohol functionalities have been reacted. The weight-average molar weight $M_w$ was increased by about 490 g/mol on the starting product.

Example 7

A mixture of 5 mmol (746 mg) of 2-hydroxyethyl N-[3'-(2"-hydroxyethyl-N'-propylcarbamoyl)]-carbamate, 100 mmol (8.61 g) of methyl acrylate, 1 g of 5 Å molecular sieve and 75 mg of Novozym 435 (lipase from *Candida antarctica* B) with 5 ml of acetone where appropriate was stirred at the stated temperature. The enzyme was removed by filtration, methyl acrylate was removed on a rotary evaporator, and 1.4 g of crude product (clear, yellowish liquid) was obtained.

A sample was taken, silylated, and analyzed by GC. According to GC analysis the composition of the product was as follows:

| Batch | Conditions | Conversion [%]a | Monoacrylate [%] | Diacrylate [%] |
|---|---|---|---|---|
| 1 | 24 h/40° C., no acetone | 62 | 84 | 16 |
| 2 | 24 h/60° C., no acetone | 90 | 57 | 43 |
| 3 | 24 h/60° C., no molecular sieve, with acetone | 82 | 93 | 7 |
| 4 | 48 h/50° C., no acetone | 98 | <2 | 98 | aConversion to monoacrylate and diacrylate in total

Example 8

A mixture of 1.0 mol (119.1 g) of hydroxypropyl carbamate (isomer mixture of 2-hydroxy-1-propyl carbamate and 3-hydroxy-2-propyl carbamate), 10.0 mol (860 g) of methyl acrylate, 172 mg of 4-methoxyphenol, 43 mg of phenothiazine, 300 g of molecular sieve (5 Å) and 9.0 g of Novozym 435 (lipase from *Candida antarctica* B) was stirred at 60° C. for 72 h. The enzyme and molar sieve were removed by filtration, methyl acrylate was removed on a rotary evaporator under reduced pressure, and 162 g of crude product (clear, colorless liquid) were obtained. A sample was taken and analyzed by GC-MS. The hydroxypropyl carbamate had reacted to an extent of 96%.

Example 9

A mixture of 5 mmol (525 mg) of 2-hydroxyethyl carbamate, 25–100 mmol of methyl acrylate, 1.0 g of molecular sieve (5 Å) and 30 mg of Novozym 435 (lipase from *Candida antarctica* B) was stirred at 60° C. for 8 h in the absence of a polymerization inhibitor. A sample was taken and analyzed by GC. The conversions of the 2-hydroxyethyl carbamate are described in the table below. The product is obtained in the form of colorless crystals.

| Methyl acrylate | | Conversion [%] with molecular sieve | Conversion [%] without molecular sieve |
|---|---|---|---|
| 50 | mmol | 85 | 80 |
| 100 | mmol | 99 | 89 |

Example 10

52.5 g of hydroxyethyl carbamate were admixed with an excess of methyl acrylate (129 g) and with 0.6 g of Fascat® 4201 E-Coat (dibutyltin oxide, Elf Atochem) and stabilizers (0.5 g of MEHQ and 0.5 g of BHT (butylated hydroxytoluene)).

Initially the mixture was stirred for 2 hours at 80° C.; the thin-layer chromatogram showed only a very low conversion. Then 18 g of molecular sieve were added. The reaction temperature was held between 90° C. and 110° C. and stirring was continued for 24 h. The molecular sieve was removed by filtration and then the excess methyl acrylate was distilled off. This gave a clear, yellow liquid which after one day began partly to crystallize.

The yield of mixture was (according to NMR) approximately 80%. A sample of the mixture was taken and was analyzed by GC-MS. In addition to the desired product (about 40% of the mixture) a series of byproducts were in evidence (e.g., glycol and acrylated glycol derivatives).

Comparative Example

A mixture of 3 mmol (1.49 g) of 2-hydroxyethyl N-[3'-(2"-hydroxyethyl-N'-propylcarbamoyl)]-carbamate, 60 mmol (5.16 g) of methyl acrylate, 0.04 g of p-toluenesulfonic acid (TSA) and 500 ppm of hydroquinone monomethyl ether for stabilization was heated to boiling under reflux. Thereafter an azeotrope of methanol and methyl acrylate was removed by distillation. After about 24 hours of reaction the mixture is cooled and the acrylated carbamate is obtained by vacuum distillation in a yield of 81%.

| Conditions | Conversion [%]a | Monoacrylate [%] | Diacrylate [%] |
|---|---|---|---|
| 24 h/comparative example with p-TSS | 81 | 61 | 12 | aConversion to monoacrylate and diacrylate in total

Coating System

The coating composition from example 7 (batch 4) was mixed with 4% by weight of Irgacure® 500 photoinitiator from Ciba Specialty Chemicals.

The mixture obtained was applied to a system consisting of cationic dipcoating, surfacer, and a basecoat (brilliant black) from BASF Coatings AG, Münster. The basecoat was predried at 80° C. for 10 minutes and exposed five times under an undoped high-pressure mercury lamp (output 120 W/cm) with a lamp-to-substrate distance of 12 cm and belt speed of 5 m/min.

The film thickness after exposure was about 50 μm.

The pendulum damping was determined in accordance with DIN 53157 and is a measure of the hardness of the coating. The result is stated in pendulum swings for a 50 μm film. High figures in this test denote high hardness.

The Erichsen cupping was determined in accordance with DIN 53156 and is a measure of the flexibility and elasticity. It is reported in millimeters (mm). High figures denote high flexibility. The adhesion with crosshatching was determined in accordance with DIN 53151 and reported as ratings. Low figures denote high adhesion.

TABLE 1

|  | Coating 1 Polyester acrylate Laromer ® PE55W without/with 20% by weight coating composition from ex. 7, batch 4 | Coating 2 Amine-modified polyether acrylate Laromer ® PO 84F without/with 20% by weight coating composition from ex. 7, batch 4 |
| --- | --- | --- |
| Exposure [mJ/cm2] | 1900 | 1900 |
| Film thickness [μm] | 55 | 60 |
| Pendulum hardness [sec] | 32/40 | 45/50 |
| Erichsen cupping after curing [mm] | 6.3/5.5 | 4.6/5.0 |
| Adhesion with crosshatching/adhesive tape removal | 5/4–5 | 5/4–5 |

TABLE 2

(Use of liquid products as reactive diluents)

|  | Coating 3 80% epoxy acrylate 20% by weight coating composition from ex. 4 | Coating 4 80% epoxy acrylate 20% by weight coating composition from ex. 7, batch 4 | Coating 5 (comp.) 80% epoxy acrylate 20% by weight hexanediol diacrylate |
| --- | --- | --- | --- |
| Exposure [mJ/cm2] | 1900 | 1900 | 1900 |
| Film thickness [μm] | 55 | 60 | 50 |
| Viscosity [Pas] | 30 | 70 | 18 |
| Pendulum hardness [sec] | 150 | 170 | 175 |
| Erichsen cupping after curing [mm] | 1.8 | 1.3 | 0.8 |
| Adhesion with crosshatching/adhesive tape removal | 5/4 | 5/4 | 5/5 |

The epoxy acrylate used is obtainable by reacting bisphenol A diglycidyl ether with acrylic acid.

The invention claimed is:

1. A process for preparing (meth)acrylic esters (F) comprising at least one urethane group comprising c) reacting an alcohol (C) comprising at least one urethane group with (meth)acrylic acid or with a saturated alcohol (D) ester of (meth)acrylic acid.

2. The process of claim 1, wherein the conversion in stage c) is set to at least 95%.

3. The process of claim 1, wherein the reaction c) is conducted at from 20 to 80° C.

4. The process of claim 1, wherein the alcohol (C) comprising at least one urethane group is obtained by a) reacting an amine (A) with a carbonate (B).

5. The process of claim 4 wherein the alcohol (C) comprising at least one urethane is obtained by a reaction comprising

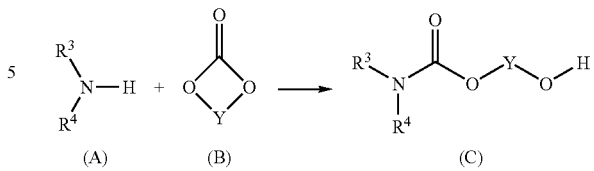

wherein $R^3$ and $R^4$ independently are hydrogen, a $C_1$–$C_{18}$ alkyl, a $C_2$–$C_{18}$ alkyl uninterrupted or interrupted by one or more oxygen and/or sulfur atoms and/or by one or more substituted or unsubstituted imino groups, or are a $C_2$–$C_{18}$ alkenyl, a $C_6$–$C_{12}$ aryl, a $C_5$–$C_{12}$ cycloalkyl or a five or a six-membered heterocycle comprising oxygen, nitrogen and/or sulfur atoms; and Y is a $C_2$–$C_{20}$ alkylene or a $C_5$–$C_{12}$ cycloalkylene or is a $C_2$–$C_{20}$ alkylene comprising one or more oxygen and/or sulfur atoms and/or one or more substituted or unsubstituted imino groups and/or one or more cycloalkyl, —(CO)—, —O(CO)O—, —(NH)(CO)O—, —O(CO)(NH)—, —(CO)— or —(CO)O— groups.

6. The process of claim 1, wherein the reaction c) is conducted in the presence of an enzyme (E).

7. The process of claim 6, wherein the enzyme (E) is a lipase, an esterase or a protease.

8. The process of claim 5, wherein $R^3$, $R^4$, or $R^3$ and $R^4$ independently are a $C_2$–$C_{18}$ alkenyl, a $C_6$–$C_{12}$ aryl, a $C_5$–$C_{12}$ cycloalkyl or a five membered heterocycle or a six-membered heterocycle comprising oxygen, nitrogen and/or sulfur atoms, and wherein at least one of $R^3$ and $R^4$ are substituted by an aryl, an alkyl, an aryloxy, an alkyloxy, at least one heteroatom, a heterocycle, a group of the formula —[$X_i$]$_k$—H, or a combination thereof; wherein k is a number from 1 to 50, and wherein $X_i$, for i=1 to k, is selected from the group consisting of —$CH_2$—$CH_2$—O—, —$CH_2$—$CH_2$—N(H)—, —$CH_2$—$CH_2$—$CH_2$—N(H)—, —$CH_2$—CH($NH_2$)—, —$CH_2$—CH(NHCHO)—, —$CH_2$—CH($CH_3$)—O—, —CH($CH_3$)—$CH_2$—O—, —$CH_2$—C($CH_3$)$_2$—O—, —C($CH_3$)$_2$—$CH_2$—O—, —$CH_2$—$CH_2$—$CH_2$—O—, —$CH_2$—$CH_2$—$CH_2$—$CH_2$—O—, —$CH_2$—CHVin-O—, —CHVin-$CH_2$—O—, —$CH_2$—CHPh—O—, and —CHPh—$CH_2$—O—, wherein Ph stands for phenyl and Vin stands for vinyl.

9. The process of claim 5, wherein the radical Y is substituted by an aryl, an alkyl, an aryloxy, an alkyloxy, at least one heteroatom, a heterocycle, or a combination thereof.

10. The process of claim 6, further comprising separating the enzyme from the reaction mixture in c) by filtration, absorption, centrifugation or decanting.

11. The process of claim 6, further comprising separating an organic solvent from the reaction mixture in c) by distillation, rectification, filtration or chromatography.

12. The process of claim 5 wherein (A) is polyethyleneimine, a hydrogenated polyacrylonitrile, a straight chain, a branched chain or a dendritic polymer having amino functions or an at least partly hydrolyzed poly-N-vinylformamide having a weight-average molecular weight Mw of from 200 to 1 000 000.

* * * * *